Figure 1:
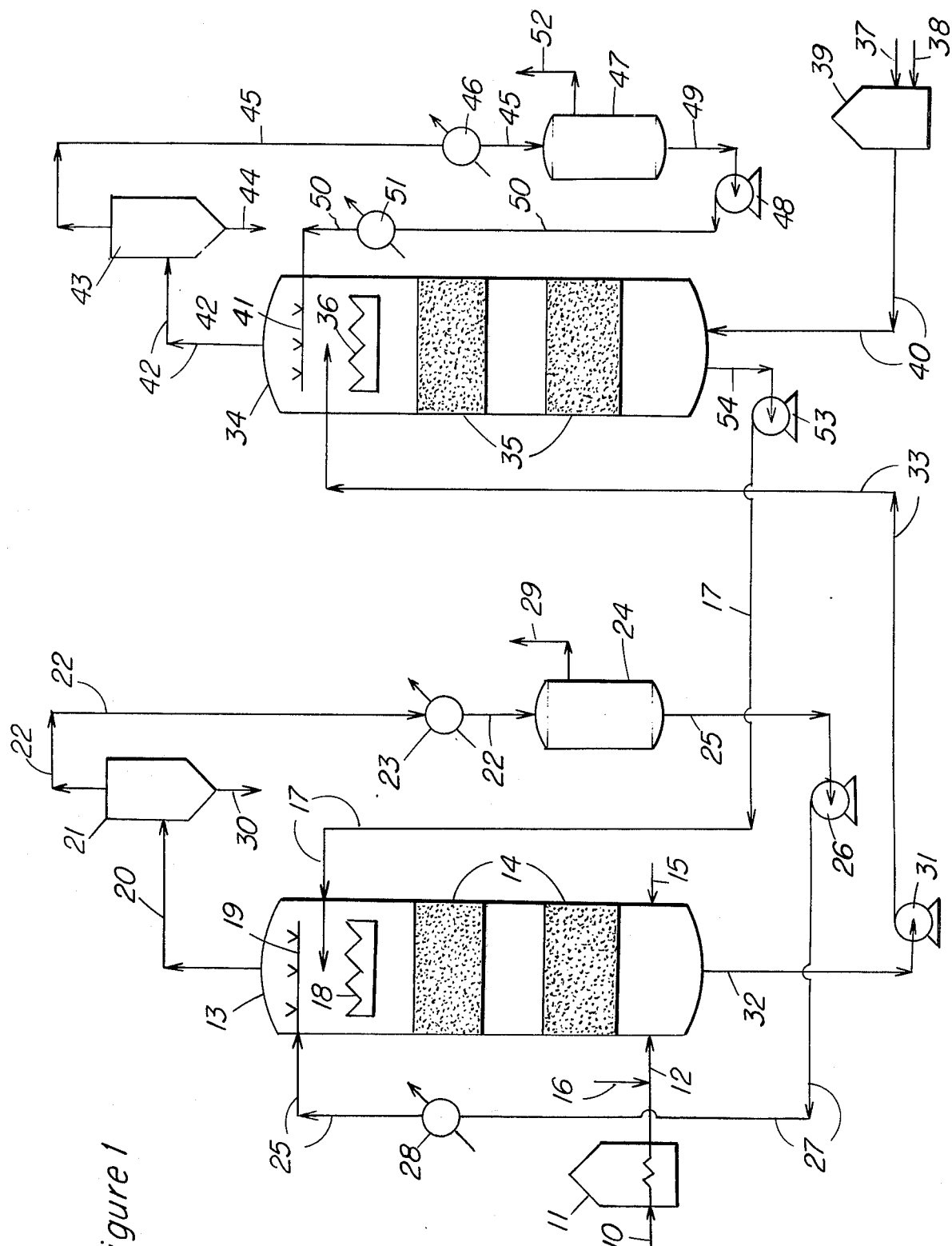

United States Patent [19]

Riegel

[11] 3,935,288
[45] Jan. 27, 1976

[54] PRODUCTION OF OLEFINIC HALIDES
[75] Inventor: Herbert Riegel, Maplewood, N.J.
[73] Assignee: The Lummus Company, Bloomfield, N.J.
[22] Filed: Dec. 2, 1970
[21] Appl. No.: 94,536

Related U.S. Application Data
[63] Continuation-in-part of Ser. No. 663,593, Aug. 28, 1967, abandoned.

[52] U.S. Cl. ............................ 260/656 R; 260/654 D
[51] Int. Cl.² ............................................. C07C 21/02
[58] Field of Search ........ 260/656 R, 654 D, 659 A, 260/DIG. 42

[56] References Cited
UNITED STATES PATENTS

| 2,140,547 | 12/1938 | Reilly | 260/656 |
| 2,378,859 | 6/1945 | Mugdan et al. | 260/656 |
| 2,407,828 | 9/1946 | Gorin | 260/659 |
| 3,291,846 | 12/1966 | Otsuka et al. | 260/656 |

FOREIGN PATENTS OR APPLICATIONS

| 705,925 | 3/1965 | Canada | 260/659 |
| 711,287 | 6/1965 | Canada | 260/659 |

OTHER PUBLICATIONS

Sundermeyer, et al., "Chemische Berichte," Vol. 95 (1962), pp. 1829–1831.

Primary Examiner—James O. Thomas, Jr.
Assistant Examiner—A. Siegel
Attorney, Agent, or Firm—Marn & Jangarathis

[57] ABSTRACT

Olefinic halides are produced by catalytic dehydrohalogenation of the corresponding saturated halide by direct contact thereof with a melt containing a multivalent metal halide in its higher and lower valence state. In particular, 1,2-dichloroethane is dehydrochlorinated to vinyl chloride by contacting thereof with a molten salt mixture of cuprous and cupric chloride at high per pass conversion and high vinyl chloride selectivity.

22 Claims, 2 Drawing Figures

PRODUCTION OF OLEFINIC HALIDES

This application is a continuation-in-part of Application Ser. No. 663,593 filed on Aug. 28, 1967 now abandoned.

This invention relates to the production of halo substituted olefinically unsaturated aliphatic hydrocarbons by the dehydrohalogenation of the corresponding saturated halide. More particularly, this invention relates to the production of vinyl chloride from 1,2-dichloroethane.

Dehydrohalogenation may be represented by the commercial process for producing vinyl chloride from 1,2-dichloroethane. In such commercial processes, 1,2-dichloroethane is dehydrochlorinated at temperatures from about 300°C. to about 600°C. in one or more reaction tubes positioned within a fired-heater reactor.

Several problems are associated with the conventional 1,2-dichloroethane dehydrochlorination. One problem is that to transfer the required endothermic reaction heat to the dichloroethane reactant intube, the tubewall must be substantially hotter than the reaction temperature intube. As a result, some coke and tar formation occurs on the hotter tube which causes additional resistance to heat transfer. This, in turn, necessitates a still higher tubewall temperature. As a consequence, the fouling of the reactor tubes frequently requires termination of operations for the purpose of cleaning the tubes. Another problem relates to the formation of acetylenic and diolefinic by-product compounds in the vinyl chloride. With increasing reaction severity — usually at once-through dichloroethane conversions in excess of about 40 percent to 50 percent — acetylenic and diolefinic compounds can form. These compounds adversely affect the polymerization of vinyl chloride and also the quality of the polymer product. Therefore the concentration of the acetylenic and diolefinic contaminants must be limited to less than about 20 ppm in the vinyl chloride monomer.

Several expedients are practiced to minimize the above difficulties, some of which entail considerable operating costs and investment. First, in order to achieve a lower reaction temperature which, in turn, permits correspondingly lower tube wall temperatures, catalytic activators such as chlorine and oxygen are introduced in small amounts with the dichloroethane feed into the reactor. Second, the tubes can be packed with a heat-conducting material such as graphite particles in a further effort to reduce the temperature differential between the tube wall and the reacting mass intube. Packing represents a cost and additionally requires extra reactor volume and presents operational difficulties with plugging of the packing. Third, the dichloroethane, feed and recycle, is subjected to careful fractionation to remove principally the heavier impurities, such as trichloroethane, which are especially prone to form coke and tars on the fired heater tube walls. With regard to acetylenic and diolefinic compounds, the vinyl chloride stream is subjected to clean-up purification in order to reduce the concentration of these contaminants to tolerable levels when necessary. Catalytic hydrogenation, chlorination or hydrochlorination is used to selectively reduce the concentration of acetylenic and diolefinic compounds. Even by resort to one or more of the foregoing expedients, the conversion per pass of 1,2-dichloroethane must still be kept to about 40–60 percent.

An object of this invention is to provide a new and improved process for dehydrohalogenating halo-substituted saturated aliphatic hydrocarbons.

Another object of this invention is to provide a new and improved process for producing vinyl chloride from 1,2-dichloroethane.

A further object of this invention is to provide a new and improved process for producing vinyl chloride from 1,2-dichloroethane at high conversion rates and with high vinyl chloride selectivity.

Figure 2:
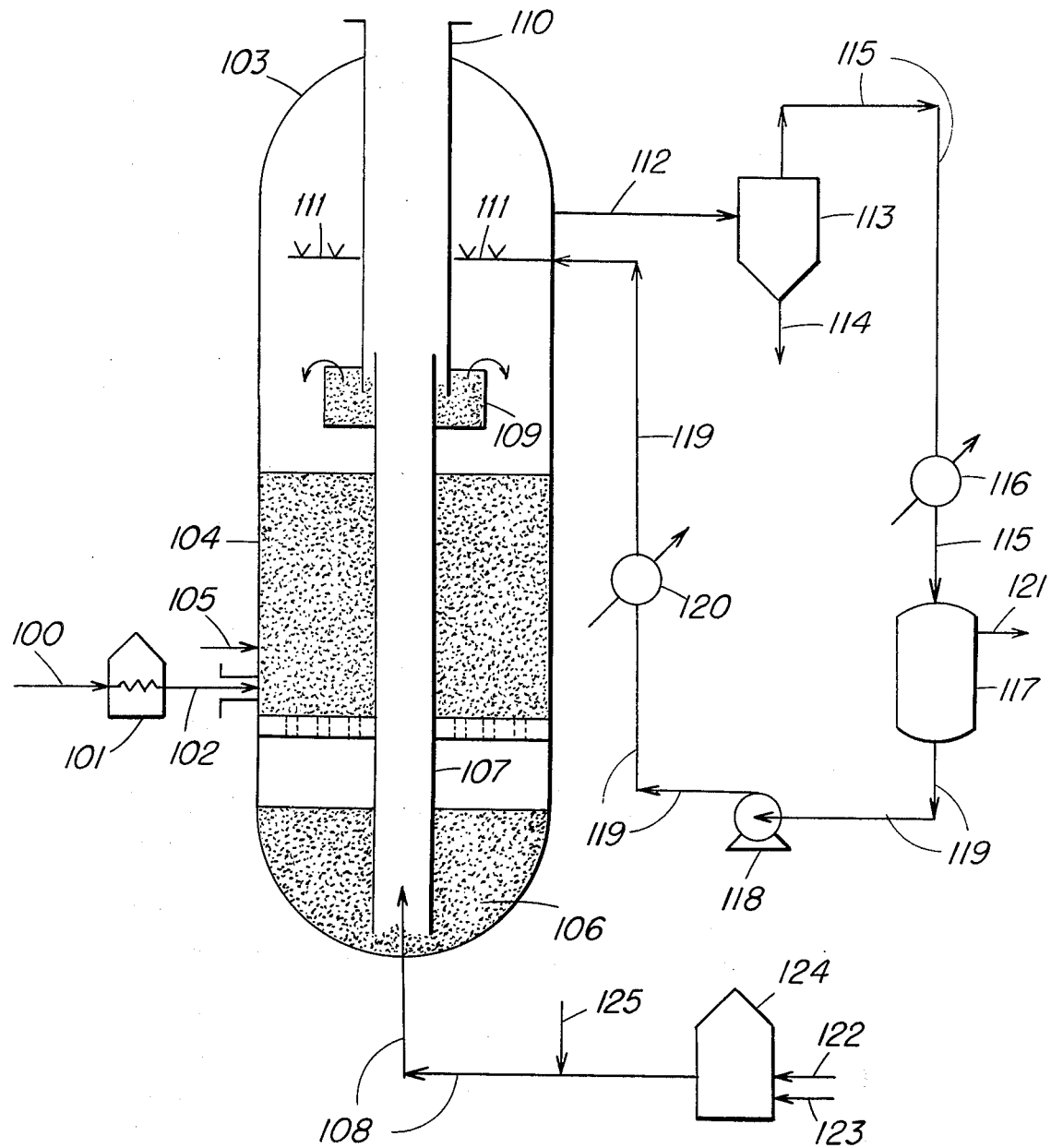

These and other objects of this invention should be readily apparent from the following detailed description thereof when read with reference to the accompanying drawings wherein:

FIG. 1 is a simplified schematic representation of a reaction system for the process of the present invention; and FIG. 2 is a simplified schematic representation of another reaction system for the process of the present invention.

The objects of this invention are broadly accomplished in one aspect by catalytically dehydrohalogenating a feed including a halo substituted saturated aliphatic hydrocarbon to the corresponding halo-substituted olefinically unsaturated aliphatic hydrocarbon by directly contacting the feed, at an elevated temperature, with a melt containing a multivalent metal halide in both its higher and lower valence state.

The objects of this invention are broadly accomplished in another aspect by producing vinyl chloride by directly contacting at an elevated temperature a feed containing 1,2-dichloroethane with a melt containing a multivalent metal in both its higher and lower valence state.

The melt contains the higher and lower valent forms of a halide of a multivalent metal; i.e., a metal having more than one positive valence state, such as manganese, iron, copper and cobalt preferably the bromides and chlorides, in particular the chlorides of the metal, with the copper chlorides being particularly preferred. In the case of higher melting multivalent metal halides, such as copper chlorides, a halide of a univalent metal; i.e., a metal having only one positive valence state which is nonvolatile and resistant to the action of oxygen under the process conditions, is added to the multivalent metal chloride to form a molten salt mixture having a reduced melting point. The univalent metal halides, the chloride and bromides, particularly the chlorides, being preferred, are preferably alkali metal chlorides, such as potassium and lithium chloride in particular, but it is to be understood that other metal chlorides and mixtures thereof, such as the heavy metal chlorides of Groups I, II, III and IV of the Periodic Table; e.g., zinc, silver, and thallium chloride, may also be employed. The univalent metal chlorides are generally added in an amount sufficient to adjust the melting point of the molten salt mixture to a temperature of below about 260°C., and in the case of a salt mixture of copper chloride and potassium chloride, the composition of the melt ranges between about 20 percent and about 40 percent, preferably about 30 percent, by weight, potassium chloride, with the remainder being copper chlorides. It is to be understood, however, that in some cases the catalyst melt may have a melting point higher than 260°C., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a univalent metal halide.

The feed is a halo-substituted saturated aliphatic hydrocarbon containing at least two halo-substituted groups, the halo-substituent preferably being chloro- or bromo-, particularly chloro-, and as representative examples of preferred feed components, there may be mentioned: 1,1-dichloroethane; 1,2-dichloroethane; 1,1,1-trichloroethane; 1,2-dichloropropane; 1,3-dichloropropane and the like. The process is particularly applicable to the production of vinyl chloride from 1,2-dichloroethane.

In accordance with one of the preferred embodiments of the process of the invention, the melt also includes, in the case of chloro-substituted feed, the oxychloride of the multivalent metal in that the oxychloride reacts with the hydrogen chloride resulting from the dehydrochlorination to provide a gaseous reaction effluent with reduced amounts, and preferably no hydrogen chloride. The reaction of the oxychloride with hydrogen chloride, using copper oxychloride as a representative example, is represented by the following equation:

(1) 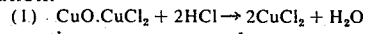 $CuO \cdot CuCl_2 + 2HCl \rightarrow 2CuCl_2 + H_2O$

In a continuous process, the copper oxychloride may be produced by oxidizing a melt containing a mixture of copper chlorides with molecular oxygen, preferably air, with the reaction being represented by the following equation:

(2) 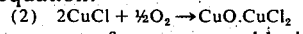 $2CuCl + \tfrac{1}{2}O_2 \rightarrow CuO \cdot CuCl_2$

The amount of copper oxychloride present in the melt is preferably sufficient to react with essentially all of the generated hydrogen chloride to provide a dehydrochlorination reaction effluent essentially free of hydrogen chloride.

The dehydrohalogenation process hereinabove described is effected at temperatures from about 300°C. to about 650°C., preferably from about 450°C. to about 500°C. and pressures from about 1 to about 20 atmospheres. The contacting is preferably effected in a countercurrent fashion, with the feed as a continuous vapor phase, at residence times from about 1 to about 60 seconds. It is to be understood, however, that other means for contacting the feed and molten salt can also be employed, including passage of the feed through a confined body of molten salt. The relative quantities of the feed and molten salt may be varied considerably, but in general, the weight ratio of salt to feed (preferably 1,2-dichloroethane) ranges from about 15:1 to about 300:1. The dehydrohalogenation reaction is endothermic and, accordingly, the molten salt acts as a heat source for the reaction. An increase in the salt to feed weight ratios decreases the temperature drop for the reaction, and the reaction proceeds more closely to isothermal conditions. The use of the hereinabove described salt to feed flow ratios for a 1,2-dichloroethane feed, preheated to a temperature of about 315°C., is generally effected with a temperature drop from about 10°C. to about 100°C.

The use of the melts hereinabove described for dehydrohalogenation, in particular for the dehydrochlorination of 1,2-dichloroethane to vinyl chloride, results in numerous benefits. The molten salt functions as a heat transfer agent which can provide both the sensible heat required to bring the feed to reaction temperature and the required endothermic heat of reaction. The use of high salt to feed ratios, as hereinabove described, results in a low temperature gradient over the length and width of the reactor, thereby eliminating the radial temperature gradients which in prior art processes cause coke and tar formation on the hotter tube walls.

The primary benefit, however, resulting from the use of melts, as hereinabove described for the dehydrochlorination of 1,2-dichloroethane to vinyl chloride, is that the molten salts catalytically directs the reaction to the production of vinyl chloride. Thus, the 1,2-dichloroethane may be converted at high rates of conversion; generally above 90 percent and approximately 100 percent conversion, while retaining high vinyl chloride selectivity, generally above 90 percent, with the reaction effluent being essentially free of diolefinic contaminations which require costly procedures to effect separation thereof from the vinyl chloride.

The invention will be further described with respect to the embodiment thereof illustrated in the accompanying drawings. It is to be understood, however, that the scope of the invention is not limited by the illustrated embodiment.

Referring to FIG. 1, 1,2-dichloroethane in line 10 at about 15 to about 300 pounds per square inch (psi) is heated and vaporized in fired heater 11 to a temperature below incipient dehydrochlorination, as from about 150°C. to about 315°C. The vaporized dichloroethane is passed via line 12 into dehydrochlorination reactor 13 which contains packed sections or equivalent vapor/liquid contacting means 14.

A molten salt of the type hereinabove described, preferably comprising cuprous chloride, cupric chloride and potassium chloride is introduced into reactor 13 through line 17 and distributor 18 at a temperature between about 315°C. and about 650°C. and the downwardly-flowing molten salt countercurrently contacts the upwardly flowing vapor feed. As a result of the direct contact between the melt and the 1,2-dichloroethane, the 1,2-dichloroethane is dehydrochlorinated to vinyl chloride.

In an upper portion of reactor 13, upflowing reaction product vapors are cooled to a temperature between about 90°C. and about 260°C. by means of equilibrium quench liquid from distributor 19 primarily to remove any entrained and vaporized salts from the effluent stream comprising reaction product. The equilibrium quench liquid comprises primarily 1,2-dichloroethane, vinyl chloride and dissolved hydrogen chloride. The combined and vaporized effluent and quench streams are withdrawn from reactor 13 via line 20, are passed to separator 21 and thence via line 22 containing cooler/condenser 23 and into vapor/liquid separator 24. Equilibrium quench liquid is withdrawn from separator 24 via line 25 by pump 26 through line 27 containing cooler 28 to distributor 19. Reaction effluent, primarily vinyl chloride, hydrogen chloride and some unconverted dichloroethane, is withdrawn from separator 24 through line 29 to conventional purification means, such as fractionators (not shown).

Salt entrained in the reaction effluent and separated in separator 21, can be removed therefrom through line 30.

Molten salt at a temperature from about 315°–650°C., and at a lower temperature than in line 17, is withdrawn from reactor 13 by means of pump 31 (or a gas lift, now shown) via line 32. It is then passed through line 33 to vessel 34, which is equipped with packed sections or equivalent vapor/liquid contacting means 35. In vessel 34, the molten salt from line 33 is passed through distributor 36 and is contacted with an upflowing stream of hot inert gas, such as nitrogen, carbon dioxide or flue gas, to provide the endothermic heat requirements expended by the molten salt in reactor 13. Preferably, the inert gas is produced by burning fuel, such as natural gas or oil, from line 37 with essentially stoichiometric air from line 38 in heater 39. The hot combustion gas is passed via line 40 into vessel 34 at a temperature between about 315°C. and about 1100°C. and at a pressure between about 15 and about 300 psi. The gas is cooled at the top of vessel 34 by quench liquid comprising essentially water from distributor 41 to a temperature of from about 40°C. to about 260°C. to remove entrained and vaporized salts from the gas effluent stream. The combined and vaporized effluent and quench streams are taken from vessel 34 through line 42 to separator 43. Entrained, separated salts can be removed from separator 43 through line 44. Vapor in line 42 and separator 43 is passed through line 45 containing cooler/condenser 46 to vapor/liquid condenser 47. Equilibrium quench liquid is withdrawn from condenser 47 by pump 48 via line 49 and is passed through line 50 containing cooler 51 to distributor 41. Waste inert gas is removed from vessel 47 via line 52 and is purified and vented.

In accordance with one embodiment of the process, the melt introduced into reactor 13 is to further include copper oxychloride to react with the hydrogen chloride generated therein, in which case, preferably, a certain amount of excess air is additionally introduced via line 38. Sufficient excess air is used to develop a sufficiently high concentration of oxygen in the hot combustion gas, entering via line 40 into vessel 34, such that at the conditions of system pressure, contact time between salt and combustion gas, and system temperature, an adequate amount of oxygen is absorbed in the molten salt as by the formation of copper oxychloride and/or copper oxide from cuprous chloride. The copper oxide and/or copper oxychloride components are conveyed in the molten salt stream (17) to vessel 13, where the oxychloride reacts with the hydrogen chloride, evolved by dichloroethane dehydrochlorination to produce cupric chloride. Alternately, the required amount of oxygen can be introduced directly into vessel 34 (by a line, not shown) or in mixture with inert gases such as nitrogen and carbon dioxide, instead of via the hot combustion gas which is the preferred method. The copper oxychloride in the melt in line 17 introduced into reactor 13 is preferably sufficient to react with essentially all of the hydrogen chloride generated therein in which case there is a net production of cupric chloride (Equation 1) which may be employed, for example, in another reactor for chlorinating a hydrocarbon.

Heated molten salt is removed from vessel 34 by pump 53 (or a gas lift, not shown) through line 54 and is passed to line 17 for use in reactor 13.

Reference is now made to FIG. 2 wherein vaporous 1,2-dichloroethane in line 100, at a pressure from about 15 to about 300 psi, is heated and vaporized in fired heater 101 to about 150°–315°C., and is then passed through line 102 into dehydrochlorination reactor 103. Reactor 103 contains packed sections or equivalent vapor/liquid contacting means 104. Upflowing dichloroethane is in countercurrent contact with downflowing molten salt in reactor 103. Molten salt from reservoir 106 positioned in the bottom of the reactor 103 is raised in lift pipe 107 by means of hot inert gas from line 108 to vapor/liquid separation section 109. The hot combustion gas in line 108 at a temperature of from about 315°C. to about 1100°C. and a pressure from about 15 to 400 psi, both lifts and heats the molten salt which circulates through the route indicated by 106-107-109-104-106. The molten salt heated by the hot gas contains sufficient heat for the dehydrochlorination and sensible heating of dichloroethane in section 104.

The lift gas flows from separation section 109 and leaves that section through vent 110; the gas can be quenched, neutralized and purified (not shown) or discarded directly. The reaction product vapors are quenched by quench liquid delivered from distributor 111. Here also, the quench liquid comprises primarily 1,2-dichloroethane, vinyl chloride and dissolved hydrogen chloride. The combined and vaporized reaction product and quench liquid is removed from vessel 103 through line 112 to separator 113. Any entrained salt in the vapor passed into separator 113 can be removed from the latter through line 114. Vapors in line 112 and separator 113 are passed through line 115 containing cooler/condenser 116 to vapor/liquid separator 117. Quench liquid is pumped from separator 117 by pump 118 through line 119 containing cooler 120 to distributor 111. Process effluent, predominantly vinyl chloride, hydrogen chloride and unconverted dichloroethane, is removed from separator 117 through line 121 and is sent to conventional purification and separation equipment.

The hot inert gas is produced preferably from fuel in line 122 and air in line 123 in heater 124, in the same manner as indicated in FIG. 1, and is passed through line 108 to lift pipe 107. If the molten salt is to also contain copper oxychloride, air or oxygen can be charged through line 125 to line 108. More preferably, the oxygen can be introduced in the form of excess air through line 123, as described for the system shown in FIG. 1. The amount of excess air is determined by the concentration of oxygen necessary in the hot combustion gas to produce the required amount of copper oxychloride and/or copper oxide from cuprous chloride in the gas lift pipe 107 under the process conditions, primarily contact time, system pressure and reaction temperature. Again, the quantities of copper oxychloride and copper oxide are determined by the hydrogen chloride produced in the dehydrochlorination zone 104.

The process of the invention will be further described with respect to the following examples, but it is to be understood that the scope of the invention is not to be limited thereby.

EXAMPLE I

An illustration of the process in connection with the system shown in FIG. 2, is provided by the following typical example.

A. 1,2-dichloroethane was passed as a vapor through line 102, molten salt was circulated by nitrogen passed through line 108, process effluent was passed through line 112, and the lift gas was withdrawn via line 110, with the process conditions and products noted below:

| | |
|---|---|
| Reaction Temperature | 470°C. |
| Reaction Pressure | 1 atm. |
| Molten Salt: | |
| KCl | 30 wt.% |
| CuCl + CuCl$_2$ | 70 wt.% |

-continued

| | |
|---|---|
| Residence time | 10 sec. |
| Duration of test | 3 hours |
| Gas Hourly Space Velocity, GHSV | 179 |
| Feed Rate, Liquid | 87 cm³/hr |
| 1,2-dichloroethane conversion | 92.4 % |

Products:

| Component | Mol % of 1,2-Dichloroethane Converted |
|---|---|
| $C_2H_3Cl$ (Vinyl Chloride) | 97.8 |
| $C_2H_5Cl$ | 0.3 |
| $C_2H_2Cl_2$ | 0.7 |
| $C_2H_3Cl_3$ | 0.6 |
| $C_2HCl_3$ | 0.2 |
| $C_2Cl_4$ | 0.4 |
| Total | 100.0 |

B. A composition, comprising 20 weight percent cupric chloride and 80 weight percent cuprous chloride, was combined with potassium chloride to provide a composition which contains 30 weight percent potassium chloride (the composition is identical to the molten composition of Part A), and the composition was placed on a finely divided alumina support (−100+200 mesh). The supported catalyst was placed in a fluidized reactor. 1,2-dichloroethane was passed through the fluidized supported catalyst at a temperature of 471°C. and a residence time of 11.5 seconds.

The conversion of 1,2-dichloroethane was 49.6 percent; and the selectivity to vinyl chloride was 83.8 percent.

The highly selective conversion of 1,2-dichloroethane to vinyl chloride at high per pass conversion achieved by using melts in accordance with the invention, as contrasted to the significantly lower conversion and selectivity, resulting from the use of solid supported copper chlorides indicates the improved and advantageous results achieved by proceeding in accordance with the present invention.

EXAMPLE II

The procedure of Example IA is repeated using the following salt composition, and a temperature of 920°F. and a residence time of 7 seconds:

| | |
|---|---|
| KCl | 34 |
| $FeCl_2$ | 58 |
| $FeCl_3$ | 8 |
| | 100 |

The effluent contains vinyl chloride.

EXAMPLE III

The procedure of Example IA is repeated using the following salt composition, and a temperature of 890°F. and a residence time of 13 seconds:

| | |
|---|---|
| LiCl | 30 |
| CuCl | 50 |
| $CuCl_2$ | 20 |
| | 100 |

The effluent contains vinyl chloride.

EXAMPLE IV

The procedure of Example I is repeated using the following salt composition, and a temperature of 930°F. and a residence time of 6 seconds:

| | |
|---|---|
| KCl | 17 |
| $MnCl_2$ | 3 |
| $MnCl_3$ | 80 |
| | 100 |

The effluent contains vinyl chloride.

EXAMPLE V

The procedure of Example I is repeated using the following salt composition, and a temperature of 930°F. and a residence time of 6 seconds:

| | |
|---|---|
| KCl | 37 |
| $CoCl_2$ | 14 |
| $CoCl_3$ | 49 |
| | 100 |

The effluent contains vinyl chloride.

The process of the present invention is extremely effective for the dehydrohalogenation of halogenated saturated aliphatic hydrocarbons; in particular 1,2-dichloroethane. The use of molten salts, as hereinabove described, results in a high per pass conversion while retaining high desired product selectivity. The processes presently known in the art are not capable of providing this combination of advantageous results.

Numerous modifications and variations of the present invention are possible in light of the above teachings and, therefore, within the the scope of the appended claims, the invention may be practised in a manner other than as particularly described.

What is claimed is:

1. A process for producing a mono-olefinically unsaturated aliphatic hydrocarbon halide by the catalytic dehydrohalogenation of the corresponding saturated halide, comprising:

directly contacting said saturated halide with a melt containing a multivalent metal halide in its higher and lower valence state, in an amount effective to catalyze the dehydrohalogenation of the saturated halide, said multivalent metal halide being selected from the group consisting of the halides of manganese, copper, iron and cobalt, said contacting being effected at a temperature from about 300°C to about 650°C, to dehydrohalogenate the saturated halide to said monoolefinically unsaturated aliphatic hydrocarbon halide.

2. The process as defined in claim 1 wherein the multivalent metal halide is selected from the group consisting of the chlorides of manganese, copper, iron and cobalt.

3. The process of claim 1 wherein the saturated halide is a chloride and the multivalent metal halide is a chloride.

4. The process as defined in claim 3 wherein said saturated olefinic halide is selected from the group consisting of 1,1-dichloroethane, 1,2-dichloroethane, 1,1,1-trichloroethane, 1,2-dichloropropane and 1,3-dichloropropane.

5. The process as defined in claim 4 wherein said multivalent metal halide is copper chloride.

6. The process as defined in claim 4 wherein the melt further includes a univalent metal halide.

7. The process as defined in claim 6 wherein the univalent metal halide is an alkali metal chloride.

8. A process for producing vinyl chloride which comprises:

directly contacting 1,2-dichloroethane with a melt containing a multivalent metal chloride in both its higher and lower valence state, in an amount effective to catalyze the dehydrochlorination of 1,2-dichloroethane to vinyl chloride, said multivalent metal chloride being selected from the group consisting of the chlorides of iron, copper, manganese and cobalt, said contacting being effected at a temperature from about 300°C to about 650°C to dehydrochlorinate the 1,2-dichloroethane to vinyl chloride.

9. The process as defined in claim 8 wherein the multivalent metal chloride is copper chloride.

10. The process as defined in claim 9 wherein the contacting is effected at a temperature from about 450°C. to about 500°C.

11. The process as defined in claim 9 wherein the melt further includes as a melting point depressant a univalent metal chloride.

12. The process as defined in claim 11 wherein the univalent metal chloride is an alkali metal chloride.

13. The process as defined in claim 9 wherein the melt further includes copper oxychloride.

14. A process for producing vinyl chloride, comprising:
directly contacting a gaseous feed consisting essentially of 1,2-dichloroethane with a melt containing cuprous and cupric chloride, in an amount effective to catalyze the dehydrochlorination of the 1,2-dichloroethane to vinyl chloride, said contacting being effected at a temperature from about 300°C to about 650°C to dehydrochlorinate the 1,2-dichloroethane to vinyl chloride.

15. The process as defined in claim 14 wherein the melt further includes as a melting point depressant a member selected from the group consisting of the alkali metal chlorides and the heavy metal chlorides of Groups I, II, III, and IV of the Periodic Table.

16. The process as defined in claim 14 wherein the melt further includes as a melting point depressant an alkali metal chloride.

17. The process as defined in claim 16 wherein the alkali metal chloride is potassium chloride.

18. The process as defined in claim 17 wherein the contacting is effected at a temperature from about 450°C. to about 500°C.

19. The process as defined in claim 18 wherein the weight ratio of the melt to 1,2-dichloroethane is from about 15:1 to about 300:1.

20. The process as defined in claim 17 wherein the melt further includes copper oxychloride.

21. The process as defined in claim 20 wherein the melt is contacted with the gaseous 1,2-dichloroethane in a first reaction zone, and further comprising: withdrawing the melt from the first reaction zone, introducing the melt into a second reaction zone and contacting the melt therein with a gas-containing molecular oxygen to produce copper oxychloride and passing the melt from the second reaction zone to the first reaction zone.

22. The process as defined in claim 21 wherein said gas-containing molecular oxygen is at an elevated temperature to provide make-up heat to the melt.

* * * * *